United States Patent
Romanoschi et al.

(10) Patent No.: US 9,949,916 B2
(45) Date of Patent: Apr. 24, 2018

(54) NON-IRRITATING LUBRICANT COMPOSITIONS WITH ACTIVE SENSORIAL AGENTS

(71) Applicant: Church & Dwight Co., Inc., Princeton, NJ (US)

(72) Inventors: Ovidiu Romanoschi, Highland Park, NJ (US); Jason R. Kieke, Freehold, NJ (US); Michael J. Harrison, Princeton, NJ (US); Luis Muniz, Brooklyn, NY (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 14/428,923

(22) PCT Filed: Oct. 2, 2013

(86) PCT No.: PCT/US2013/063019
§ 371 (c)(1),
(2) Date: Mar. 17, 2015

(87) PCT Pub. No.: WO2014/055621
PCT Pub. Date: Apr. 10, 2014

(65) Prior Publication Data
US 2015/0250704 A1     Sep. 10, 2015

Related U.S. Application Data

(60) Provisional application No. 61/709,460, filed on Oct. 4, 2012.

(51) Int. Cl.
| | |
|---|---|
| *A61K 8/891* | (2006.01) |
| *A61K 8/898* | (2006.01) |
| *A61K 8/892* | (2006.01) |
| *A61K 8/895* | (2006.01) |
| *A61K 8/34* | (2006.01) |
| *A61Q 19/00* | (2006.01) |
| *A61F 6/04* | (2006.01) |
| *A61K 8/58* | (2006.01) |
| *A61K 9/00* | (2006.01) |

(52) U.S. Cl.
CPC .............. *A61K 8/891* (2013.01); *A61F 6/04* (2013.01); *A61K 8/34* (2013.01); *A61K 8/347* (2013.01); *A61K 8/585* (2013.01); *A61K 8/892* (2013.01); *A61K 8/895* (2013.01); *A61K 8/898* (2013.01); *A61Q 19/005* (2013.01); *A61K 9/0014* (2013.01); *A61K 2800/242* (2013.01); *A61K 2800/244* (2013.01); *A61K 2800/31* (2013.01); *A61K 2800/594* (2013.01)

(58) Field of Classification Search
CPC .......... A61K 8/34; A61K 8/585; A61K 8/891; A61K 8/892; A61K 8/895; A61K 8/898; A61K 9/0014; A61K 2800/242; A61K 2800/244; A61K 2800/31; A61K 2800/594; A61F 6/04; A61Q 19/005
USPC .......................................................... 424/704
See application file for complete search history.

(56) References Cited

U.S. PATENT DOCUMENTS

| | | | |
|---|---|---|---|
| 6,780,443 B1 | 8/2004 | Nakatsu et al. | |
| 7,005,408 B2 | 2/2006 | Ahmad et al. | |
| 7,030,273 B1 | 4/2006 | Sun | |
| 7,285,517 B2 | 10/2007 | Ahmad et al. | |
| 7,405,186 B2 | 7/2008 | Harrison | |
| 7,417,013 B2 | 8/2008 | Ahmad et al. | |
| 7,658,941 B2 | 2/2010 | Ahmad et al. | |
| 7,695,730 B2 | 4/2010 | Ahmad et al. | |
| 7,726,487 B2 | 6/2010 | Ahmad et al. | |
| 7,758,887 B2 | 7/2010 | Ahmad et al. | |
| 7,851,419 B2 | 12/2010 | Ahmad et al. | |
| 2006/0159645 A1 | 7/2006 | Miller et al. | |
| 2006/0269500 A1 | 11/2006 | Riemer et al. | |
| 2007/0281008 A1* | 12/2007 | Lin | A61K 9/0036 424/456 |
| 2008/0193492 A1 | 8/2008 | Ahmad et al. | |
| 2009/0028811 A1* | 1/2009 | Potter | A61K 9/0034 424/78.02 |
| 2009/0054497 A1 | 2/2009 | Ahmad et al. | |
| 2009/0054498 A1 | 2/2009 | Ahmed et al. | |
| 2009/0197982 A1 | 8/2009 | Miyagawa et al. | |
| 2010/0012132 A1* | 1/2010 | Harrison | A61F 6/04 128/844 |
| 2011/0237674 A1 | 9/2011 | Zhang et al. | |

FOREIGN PATENT DOCUMENTS

| | | |
|---|---|---|
| EP | 0475664 B1 | 11/1993 |
| EP | 0 988 852 A2 * | 3/2000 |

OTHER PUBLICATIONS

Viscosity Conversion Chart: retrieved from internet: http://www.engineeringtoolbox.com/viscosity-converter-d_413.html. Retrieved on Mar. 7, 2016.*
K-Y yours & mine product: retrieved from internet: http://web.archive.org/web/20090610170242/http://www.bearabledeals.com/reviews/kyreview.htm. Retrieved on Nov. 10, 2016.*
K-Y Brand Intrigue: retrieved from internet: https://www.accessdata.fda.gov/cdrh_docs/pdf6/K062796.pdf. Retrieved on May 1, 2017.*
Supplementary European Search Report, dated Apr. 1, 2016, pp. 1-8 for EP13843490.7, which corresponds to this present application.
Supplementary European Search Report, dated Feb. 29, 2016, pp. 1-6 for EP1384405.4, which corresponds to this present application.

* cited by examiner

*Primary Examiner* — Hong Yu
(74) *Attorney, Agent, or Firm* — Church & Dwight Co., Inc.

(57) ABSTRACT

A non-irritating personal lubricant composition comprises a silicone fluid carrier and at least one sensorial agent, the composition having a viscosity of at least 175 centistokes.

10 Claims, No Drawings

NON-IRRITATING LUBRICANT COMPOSITIONS WITH ACTIVE SENSORIAL AGENTS

FIELD OF THE INVENTION

This invention is directed to non-irritating personal lubricant compositions with functional sensorial agents.

BACKGROUND OF THE INVENTION

Personal lubricants for intimate contact are well known. In recent years, it has become increasingly popular to add various functional agents to personal lubricant compositions in order to, for example, enhance pleasurable feelings during sexual activity and/or to heighten sexual arousal. Examples of such products include K-Y® Warming Liquid and Durex® Play Tingling. K-Y® Warming Liquid is a water-soluble, anhydrous composition that warms on contact while providing lubrication. Durex® Play Tingling is a water-soluble composition with a unique blend of agents that warms, cools and tingles while providing lubrication.

Using condoms containing lubricants which include sensorial agents has also been proposed. Producing such lubricated condoms is somewhat challenging, particularly if the lubricant is to be applied both on the inside and on the outside of the condom. Conventional machinery used in condom manufacture mandates that the lubricant composition have relatively tight specifications, for example, in terms of viscosity, tackiness and stringiness, as well as providing the desired degree of lubricity.

Personal lubricants comprising functional agents are designed to cause physiological or physical changes in the area to which they are applied. These functional agents range from agents that self-warm when exposed to moisture, e.g. polyols, agents that act on nerve endings to simulate a perceived sensation such as warming, cooling and/or tingling, and agents that could in sufficient quantity increase localized blood flow, e.g. vasodilators.

Self-warming lubricants are known in the art. They generate heat or warming when placed in contact with moisture on the human body, e.g. K-Y® Warming Liquid. The warming effect is created by a phenomenon known as heat of dilution; some agents when diluted with water release energy in the form of heat; e.g., polyethylene glycol. When blended with an anhydrous composition, the product upon dilution provides a slight warming effect.

Thermoreceptors belong to the class of transient receptor potential (TRP). TRP subfamily V, members 1 to 3 (TRPV1 to TRPV3) are activated by heat. TRPV4, TRP subfamily A, member 1 (TRPA1) and TRP melastatin 8 (TRPM8) are activated by cold. The cold receptor TRPA1 when activated by noxious cold produces a pain-like sensation, which paradoxically produces a human sensorial effect often described as "hot".

Lubricants that provide a perceived sensation are also known in the art. For example, Trojan® Fire & Ice® condom comprises a lubricant composition on the condom that utilizes vanillyl butyl ether (VBE) to simulate a perceived warming sensation and menthol to simulate a perceived cooling sensation. Chemical warming agents (such as VBE) bind TRPV1 on sensory neurons. Chemical cooling agents (such as menthol) bind to TRPM8 or cold and menthol receptor 1 (CMR1).

However, some agents like VBE, menthol, vasodilators, and various natural extracts, e.g. sichuan, jambu, ginger, maca, etc., are known to be skin irritants. Such compositions have the disadvantage of causing irritation to the mucosa, which can be problematic in relation to the vaginal or oral mucosa as irritation may disrupt the sexual experience. Accordingly, there remains a need to deliver a sensory stimuli using a personal lubricant while minimizing the effect of irritation.

PRIOR ART

K-Y® INTENSE®—a water-soluble arousal gel that uses a vasodilator (niacin) as an active ingredient.

US Patent Pub: 20090197982 "Anhydrous Compositions Useful for Attaining Enhanced Sexual Wellness"

US Patent Pub: 20090054498 "Anhydrous Compositions Useful for Attaining Enhanced Sexual Wellness"

US Patent Pub: 20090054497 "Method for Attaining Enhanced Sexual Wellness Using Anhydrous Composition"

K-Y® YOURS+MINE®—dual lubricant system; lubricant #1 uses a water-soluble anhydrous composition with self-warming agents (glycols), lubricant #2 is water-soluble with chemical cooling agents (Menthyl Lactate, Methyl Salicylate)

U.S. Pat. No. 7,726,487 "Complementary Personal Lubricant Compositions"

US Patent Pub: 20080193492 "Complementary Personal Lubricant Compositions"

K-Y® WARMING® Jelly—water-soluble anhydrous composition with self-warming agents (glycols)

K-Y® WARMING® Liquid—water-soluble anhydrous composition with self-warming agents (glycols)

K-Y® TINGLING® Jelly—water-soluble lubricant with chemical cooling agents (Menthyl Lactate, Methyl Salicylate)

K-Y® INTRIGUE® HEAT™—VBE in silicone fluid @ viscosity of about 125 centistokes

U.S. Pat. No. 7,851,419 "Substantially Anhydrous Sprayable Personal Lubricant"

U.S. Pat. No. 7,758,887 "Warming and Nonirritating Lubricant Compositions and Method of Comparing Irritation"

U.S. Pat. No. 7,695,730 "Warming and Nonirritating Lubricant Compositions and Method of Comparing Irritation"

U.S. Pat. No. 7,658,941 "Warming and Nonirritating Lubricant Compositions and Method of Comparing Irritation"

U.S. Pat. No. 7,417,013 "Warming and Nonirritating Lubricant Compositions and Method of Comparing Irritation"

U.S. Pat. No. 7,285,517 "Warming and Nonirritating Lubricant Compositions and Method of Comparing Irritation"

U.S. Pat. No. 7,005,408 "Warming and Nonirritating Lubricant Compositions and Method of Comparing Irritation"

Durex® Play® Utopia®—water-soluble arousal gel that uses a vasodilator precursor (Arginine HCl) as an active ingredient and a chemical cooling agent (isopulegol)

Durex® Play® Warmer®—water-soluble lubricant with self-warming agents (glycols)

Durex® Play® Tingling®—water-soluble lubricant with a flavor

LifeStyles® Warm Loving—water-soluble lubricant with self-warming agents (glycols)

LifeStyles® Excite—water-soluble arousal gel that uses a vasodilator precursor (L-Arginine) as an active ingredient and a chemical cooling agent (menthol)

SUMMARY OF THE INVENTION

The present invention provides a personal lubricant composition that includes (a) at least one silicone-containing component as a fluid carrier, and (b) at least one sensorial agent selected from warming, cooling, tingling or vasodilation agents. The silicone-containing fluid component may be selected from, for example, cyclomethicone, cyclopentasiloxane, and dimethicone, and mixtures thereof.

Also provided is a method of moderating the effect of a functional sensorial agent (e.g., a tingling, cooling or warming agent), comprising adding the sensorial agent to a silicone-containing fluid component as a carrier for the sensorial material.

DETAILED DESCRIPTION OF THE INVENTION

The effect of sensorial agents is moderated when combined with a carrier fluid comprising silicone (e.g. dimethicone), instead of aqueous-based carriers. It has also been found that skin irritation or even adverse affects of the sensorial agent are moderated using silicone as the carrier for the sensorial agent. The sensorial agents of this invention can include warming, cooling or tingling agents, as well as vasodilating agents.

Warming Agents

As used herein warming agents refer to compounds that impart heating or warming sensation upon topical application to the skin, oral cavity, throat or mucous membrane. Warming agents may be selected from the group consisting of capsaicin, gingerol, vanillyl ethyl ether, vanillyl propyl ether, vanillyl butyl ether, vanillyl pentyl ether, vanillyl hexyl ether, vanillyl butyl ether acetate, 4-(1-menthoxymethyl)-2-phenyl-1,3-dioxolan, 4-(1-menthoxymethyl)-2-(3',4'-dihydroxyphenyl)-1,3-dioxolan, 4-(1-menthoxymethyl)-2-(2'-hydroxy-3'-methoxyphenyl)-1,3-dioxolan, 4-(1-menthoxymethyl)-2-(4'-methoxyphenyl)-1,3-dioxolan, 4-(1-menthoxymethyl)-2-(3',4'-methylenedioxyphenyl)-1,3-dioxolan, 4-(1-menthoxymethyl)-2-(3'-methoxy-4'-hydroxyphenyl)-1,3-dioxolan, red, pepper oil, red pepper oleoresin, ginger oleoresin, nonylic acid vanillyl amide, *Spilanthes acmella* extract, *Zanthoxylum alatum* extract, *Zanthoxylum piperitum* extract, sanshool I, sanshool II, sanshoamide, black pepper extract, chavicine, piperine, spilanthol, or those warming agents disclosed in U.S. Pat. No. 6,780,443, which is hereby incorporated by reference in its entirety.

As would be understood by one of ordinary skill in the art, the same compound may act differently depending on its, use level in the composition. For example, a compound may act as a warming agent at a certain use level, yet the same compound will act as a tingling sensorial agent at a higher use level.

Cooling Agents

When cooling agents (also known as cooling sensates) are added to compositions containing warming agents, the cooling agent increases the warming effect of the warming agent. See, e.g. U.S. Pat. No. 6,780,443 which is hereby incorporated by reference. Accordingly, topical warming compositions of the present invention may contain a "cooling agent".

In embodiments in which a warming effect is desired, the compositions should contain higher amounts of warming agents than cooling agents.

It has also been found that topical cooling compositions containing a cooling agent (and smaller amounts or no warming agent) increase the cooling effect of the cooling agent. Therefore, the present invention also provides compositions that include a cooling agent contained in a silicone-containing fluid carrier. These compositions contain a majority of a cooling agent, based on the total amount of sensorial agents added to the composition.

Cooling agents which may be included in compositions of the present invention include, but are not limited to, menthol, menthone, camphor, pulegol, isopulegol, cineol, mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethane-1-ol, 3-1-menthoxpropane-1-ol, 4-1-menthoxybutane-1-ol, 1-(2-hydroxy-4-ethylcyclohexyl)-ethanone, menthyl 3-hydroxybutanoate, menthyl lactate, menthone glycerin ketal, 2-(2-1-menthyloxyethyl)ethanol, menthyl glyoxylate, N-methyl-2,2-isopropylmethyl-3-methylbutanamide, menthyl 2-pyrrolidone-5-carboxylate, monomenthyl succinate, alkali metal salts of monomenthyl succinate, and alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)cyclohexyl]carbonyl]glycine, p-menthane-3-carboxylic acid glycerol ester, Menthol propylene glycol carbonate; Menthol ethylene glycol carbonate, and 6-isopropyl-3,9-dimethyl-1,4-dioxaspiro[4.5]decan-2-one.

Other cooling agents are disclosed in U.S. Pat. Nos. 7,030,273 and 6,780,443, which are hereby incorporated by reference in their entirety.

For example, a compound may act as a cooling agent at a certain use level, yet the same compound will act as a tingling sensorial agent at a higher use level. In particular, this is true for menthol and menthol derivatives.

In other embodiments of the present invention, sensorial agents besides warming agents and cooling agents are added to a silicone-containing component in order to enhance the sensorial material. For example, in one embodiment of the present invention a tingling agent is added to a silicone-containing component to enhance the tingling effect of the sensorial material.

Silicone-Containing Component

Compositions of the present invention comprise a silicone-containing fluid carrier, which is essentially water free. Although the silicone-containing fluid carrier, per se, does not generally yield a warming or cooling effect when topically applied, it appears to moderate the warming or cooling effect of known sensorial agents compared to aqueous-based carriers. Similarly, the silicone-containing fluid carrier reduces any irritation known to be caused by warming or cooling agents, which are directed to the skin or mucosa by aqueous carriers.

Examples of silicone-containing fluids that may be used in compositions of the present invention include, but are not limited to, polymers based on methyl silicones, such as cyclomethicone and dimethicone; siloxanes, such as cyclopentasiloxane. Cyclomethicone and Dimethicone Copolyol (DC 5225 C and DC 3225 available from Dow Corning) and Cyclopentasiloxane & Dimethicone Copolyol (GE SF 1528) may also be used as a silicone-containing component of the present invention.

Preferably, although not invariably, the silicone component of the present compositions often comprises a dimethicone (trimethyl siloxane-terminated polydimethylsiloxane) or phenyltrimethicone component. Additional or alternative silicones may be present; these additional or alternative silicone components may include one or more of the following: a dimethiconol (hydroxy-terminated polydimethylsiloxane) component, a cyclopentasiloxane component, a dimethicone/vinyl dimethicone cross-polymer component. For example, a silicone component may be a D5 cyclic or small linear dimethicone, disiloxane vinyl cross polymer.

In one embodiment, the amount of silicone-containing carrier fluid is at least 98% by weight, preferably at least 99% by weight, more preferably at least 99.5% by weight of the total composition. The fluid carrier is essentially water free, and is preferably anhydrous. As shown in the examples, compositions of the present invention may include a combination of one or more sensorial agents of the same type. For example, the compositions may contain a mixture of warming agents. On the other hand, a mixture of sensorial agents having differing affects may be used, e.g. warming and cooling agents. The selection of the sensorial agent combinations may be adjusted to fine-tune the intensity and duration of the sensation desired. In addition, time-release effects may be achieved by certain sensorial agent combinations, or by treatment of sensorial agents such as by encapsulation methods and the like, to provide extended solubility in the base composition.

An important feature of the personal lubricants of this invention is the ease with which the lubricant can be applied, and the ability of the lubricant to be maintained on the area of skin and/or mucosa once it has been applied. The lubricant of this invention can also be readily applied and maintained on the inside and/or outside surfaces of condoms and personal sensorial devices. Thus, the viscosity of the personal lubricant is controlled by manipulating the molecular weights and ratios of any different silicone fluids used as the fluid carrier. Thus, the molecular weights of the silicone fluids utilized and the ratios of any different types of silicone fluids utilized need to yield a viscosity of at least 175 centistokes. Viscosities of at least 200 centistokes are also useful. A typical maximum viscosity would be between about 500 to 700 centistokes. In addition, if the composition of this invention is used as a condom lubricant, the viscosity of the silicone carrier should preferably be between about 180 to 220 centistokes, with 190 to 210 centistokes preferred.

EXAMPLES

The prior art has focused on the incorporation of various functional agents into personal lubricant compositions that are water-based or water-soluble, in order to enhance pleasurable feelings during sexual activity, and/or to heighten sexual arousal. However, the prior art does not teach how to formulate a lubricant composition that is deemed non-irritating by virtue of the addition of the functional agents, in the absence of insulating agents, encapsulation, or controlled dosage.

In this example, various lubricant prototypes were assessed to understand strengths and weaknesses of each as a stand-alone lubricant for use with a partner and for self-masturbation.

Methodology:

In the study, participating couples were randomly assigned to one of four cells. In each cell, couples were given water-based lubricant with no functional agents (K-Y® Natural Feeling Liquid) to use as a control product. Both the male and female partner used the control product during multiple sexual experiences. The couples then filled out questionnaires about the control product (couples were instructed not to discuss their answers to the questions with each other).

No adverse reactions were observed in this study.

After submitting their responses for the control product, couples were given one of four test products and repeated the procedure. The test products are set forth in Table 1 below. Couples in row 1 were provided Prototype A; couples in row 2 were provided Prototype B; couples in row 3 were provided Prototype C; couples in row 4 were provided Prototype D. A total of 84 couples completed the study, with 21 couples in row 1, 22 couples in row 2, 23 couples in row 3, and 18 couples in row 4.

TABLE 1

| Product ID | Base Composition | Functional agents |
|---|---|---|
| Prototype #623 | Silicone-Based | 0.06% Menthol and 0.01% VBE |
| Prototype #732 | Silicone/Water Based "Hybrid" | 0.06% Menthol and 0.01% VBE |
| Prototype #125 | Water-Based (~90% water content) | 0.01% VBE, 0.05% Hexyl Nicotinate, 0.01% Ginger, 0.01% Maca, 0.01% L-Arginine |
| Prototype #352 | Water-Based (~60% water content) | 0.01% VBE, 0.05% Hexyl Nicotinate, 0.01% Ginger, 0.01% Maca, 0.01% L-Arginine |

TABLE 2

| Prototype # 623 Ingredients RT Product Number | % w/w Improved Silicone with VBE + Menthol 623 |
|---|---|
| Cosmetic Fluid 2006-OH[1] | 99.93 |
| Vanillyl Butyl Ether, Food Grade | 0.01 |
| DL-Menthol | 0.06 |
| Total | 100.00 |

[1]ChemSil Silicones, Inc.
>60% Dimethylpolysiloxane
5-15% Dimethylpolysiloxane, Hydroxyl-terminated

TABLE 3

| Prototype # 732 Ingredients RT Product Number | % w/w Hybrid with VBE + Menthol 732 |
|---|---|
| Deionized Water | 30.93 |
| Propylene Glycol, USP | 52.00 |
| DL-Menthol, USP | 0.06 |
| Vanillyl Butyl Ether | 0.01 |
| Emulsil WSL-CF[1] | 17.00 |
| Propylene Glycol, USP | Q.S.* |
| Total | 100.00 |

[1]ChemSil Silicones, Inc.
80-90% Dimethylpolysiloxane
5-15% Reaction product of dimethyl siloxane, vinyl-terminated and dimethyl, methyl-hydrogen siloxane
2-8% 2-Propenoic acid, 2-hydroxyethyl ester polymer with 2-methyl-2-[(1-oxo-2-propenyl) amino]-1-propanesulfonic acid monosodium salt

TABLE 4

| Prototype #125 Ingredients RT Product Number | % w/w Water Based 90% 125 |
|---|---|
| Deionized Water | 93.58 |
| Methylparaben, NF | 0.10 |
| Propylparaben, NF | 0.05 |
| Sodium Hyaluronate | 0.50 |
| Hydroxyethylcellulose | 0.50 |
| Lactic Acid, 88% | 0.26 |
| Urea | 1.00 |
| Glycerin, USP | 2.00 |
| Citric Acid | 0.10 |
| Sodium Citrate, USP | 0.47 |
| Sodium Chloride | 0.35 |
| Ginger LE | 0.01 |
| MACA LE | 0.01 |
| L-Arginine | 0.01 |
| Vanillyl Butyl Ether | 0.01 |
| Hexyl Nicotinate | 0.05 |
| Polysorbate 60 | 1.00 |
| Total | 100.00 |

TABLE 5

| Prototype # 352 Ingredients RT Product Number | % w/w Water Based 60% 352 |
|---|---|
| Deionized Water | 58.28 |
| Polyquaternium-7 (Mirapol 550) | 5.00 |
| Propylene Glycol, USP | 5.00 |
| Methylparaben, NF | 0.10 |
| Propylparaben, NF | 0.05 |
| Citric Acid, Anhydrous, Granular, USP | 0.08 |
| Sodium Citrate Dihydrate, USP | 0.05 |
| Glycerin, USP | 30.00 |
| Hydroxyethyl Cellulose (Natrosol 250HX PHARM) | 0.35 |
| Vanillyl Butyl Ether, Food Grade | 0.01 |
| Polysorbate-60 | 1.00 |
| Hexyl Nicotinate | 0.05 |
| Ginger | 0.01 |
| aca | 0.01 |
| L-Arginine | 0.01 |
| Total | 100.00 |

Summary of Key Findings

Prototype A:
Overall
The warming (sometimes tingling/cooling) sensations contributed to favorable reactions to this lubricant, and heightened the overall experience for a number of men and women.
Sensations
A warming sensation was experienced by many as a comfortable warming, and was not too hot. There was no burning at any point. The sensation gradually increased in warmth after application. This increased pleasure when used for both self-masturbation as well as with partner. Some also felt a pleasurable and not too extreme tingling or cooling sensation, either right after application and/or during intercourse.

Only a very few (2 women for solo and partnered sex, 1 woman for solo sex) did not feel any sensations, but were very positive about this lubricant due to its superior lubrication qualities.

Prototype B:
Overall
Reactions were highly polarized: respondents were either very negative to the intense sensations or liked it very much.
Sensations
Over half of the women and men in this study found this lubricant too hot and burning, especially when used with a partner, and strongly disliked this lubricant. It was so intense that it curtailed the sexual experience for some. A few men found this tolerable (although not ideal), yet most would not continue to use it since it was "overwhelmingly hot" for their partners. Some also felt a tingling or cooling sensation.

The remaining women (less than half) were favorable towards this lubricant, because it had an intense, pleasurable tingling, warming, or cooling sensation. All of these women indicated that they preferred sensation producing lubricants, prior to the test. It had no or very little sensation, but was a very good lubricant.

Prototype C:
Overall
There was a very wide range of reactions to the sensations generated by this lubricant.
Sensations
Some found it warm. The warmth seemed to gradually build for most, which added enjoyment to the sexual experience for some. Some would have liked the warming sensation to last longer. They reported it lasted from 2 to 5 minutes. Some reapplied the lubricant to re-ignite the warming feeling. A few mentioned feeling a warming, tingling, cooling sensation. Some found it too hot or burning (more so women), usually for a short period of time—from a "brief spike" (for men, burning at penis tip or in urethra) to a few minutes (for women, internally). This got in the way of achieving an orgasm and/or enjoying sex. Some women noted that the intense warming or burning sensation eased after about 2-5 minutes, but did not go away completely for up to 15-25 minutes. A few felt no sensation or only a very slight warming.

Prototype D:
Overall
Most men and women had very negative reactions to this prototype. Many said it was "too hot"/"burning", particularly when used with a partner.
Sensations
There was very uncomfortable "heat" and "burning" for many during partnered sex, especially for women. Burning/heat was said to get even more intense for some women during penetration/intercourse due to friction, which was very distracting. For a few, the extreme sensation interrupted the sexual experience and/or made it so that the man/woman couldn't reach orgasm. A few men felt that the level of warmth was acceptable for themselves, but that their partner felt it to be too warm/hot and uncomfortable. A few women also said that the lubricant was warm, not hot, and increased/lengthened arousal when used solo. The burning/warmth lasted too long for many: up to 30 minutes for women, 5 minutes for men.

Results:
The quantitative data from the study revealed a consistent trend of prototype A outperforming the other test products, with prototype B receiving the next best scores, followed by prototype C, and then prototype D.

For some questions, such as questions identifying levels of irritation (non-adverse reaction), responses for the control product were consistent across all cells. These questions showed a trend that prototype A outperformed prototype B, which outperformed prototype C, which outperformed prototype D.

For questions identifying the perception of a sensation, responses for the control product were consistent across all cells. For responses for the question "did you feel a sensation from the lubricant?," the control product received consistently low scores (lack of sensation), while the scores for the four test products demonstrated a perceived sensation.

Those respondents indicating a sensation was felt with the test lubricant were asked to select the type of sensation felt from a list of options: burning, warming, cooling, irritation, numbing, tingling and other. A burning sensation was associated predominately with products C and D, followed by product B, whereas fewer respondents, both in absolute numbers and as a proportion of those who felt a sensation, associated product A with a burning sensation, compared to products C, D and B.

Upon closer inspection of negative sensations, such as burning and irritation, product D displayed the highest percentage of respondents reporting burning and irritation. Product A displayed the lowest percentage of respondents reporting burning and irritation, compared to products D, C, and B.

For respondents indicating that a sensation was felt with the test lubricant, respondents were asked to identify the onset of a sensation from a list of options: immediately (less than one minute), within 1-5 minutes, within 6-10 minutes, or after more than 10 minutes. The mean onset of sensation was perceived more quickly with products C and D, relative to products A, B and the control.

Compiling the results of all of the tested products, the onset of the sensations of irritation, numbing, and burning occur later, compared to the other sensations.

Finally, respondents were asked to identify the duration of the sensation from a list of options: a lot less time than desired, a little less time than desired, about the right time as desired, a little longer than desired and a lot longer time than desired. Product D received a higher average score than product A and the control, indicating, a longer-than-desired effect. Compiling the results of all of the tested products, negative sensations of burning, irritating, and numbing all had high average scores, indicating a longer-than-desired effect. The sensations cooling, tingling, and warming all had scores close to the desired length of time. Specifically, product B had an overall polarizing response with some negative responses to intense sensations. Similarly, product D had an overall negative qualitative response to intense sensations, primarily during intercourse.

CONCLUSION

Product A received consistently outperforming scores over the other test products, whereas products C and D received, consistently lower-performing scores than the other test products.

The invention claimed is:
1. An anhydrous silicone-based lubricant composition comprising 1) a silicone fluid carrier comprising a combination of at least 60 wt. % of dimethylpolysiloxane, and 5-15 wt. % of hydroxyl-terminated dimethylpolysiloxane, based on the total weight of said silicone fluid carrier; and 2) at least one sensorial agent, said composition having a viscosity of between 400 to 800 centistokes, and said silicone fluid carrier present in an amount of at least 98 wt. % of said composition, wherein said lubricant composition is a non-encapsulated lubricant composition.

2. The composition of claim 1, having a water content of less than 2.0 wt. %.

3. The composition of claim 1, wherein said at least one sensorial agent includes a warming agent.

4. The composition of claim 1, wherein said at least one sensorial agent includes a cooling agent.

5. The composition of claim 1, wherein said at least one sensorial agent includes a mixture of at least one warming agent and at least one cooling agent.

6. The composition of claim 5, wherein said warming agent is vanillyl butyl ether and said cooling agent is menthol.

7. The composition of claim 1, wherein said silicone, fluid carrier comprises at least 99 wt. % of said composition.

8. The composition of, claim 1, wherein said silicone fluid carrier comprises at least 99.5 wt. % of said composition.

9. A condom having an anhydrous silicone based lubricant composition placed on either an outside portion, an inside portion or both of said portions, wherein said lubricant composition comprises 1) a silicone fluid carrier comprising at least 60 wt.% of dimethylpolysiloxane, and 5-15 wt.% of hydroxyl-terminated dimethylpolysiloxane based on the total weight of said silicone fluid carrier; and 2) at least one sensorial agent, said composition having a viscosity of between 400 to 800 centistokes, and said silicone fluid carrier present in an amount of at least 98 wt. % of said composition, wherein said lubricant composition is a non-encapsulated, lubricant composition.

10. The condom of claim 9, wherein said at least one sensorial agent includes a warming agent and a cooling agent.

* * * * *